United States Patent [19]

Dunn

[11] 4,066,762

[45] Jan. 3, 1978

[54] DERIVATIVES OF 7-(2-SUBSTITUTED-2-HYDROX-YIMINOACETAMIDO)-3-(1-SUBSTITUTED TETRAZOL-5-YLTHIOMETHYL-3-CEPH-EM-4-CARBOXYLIC ACID

[75] Inventor: George Lawrence Dunn, Wayne, Pa.

[73] Assignee: SmithKline Corporation, Philadelphia, Pa.

[21] Appl. No.: 704,160

[22] Filed: July 12, 1976

[51] Int. Cl.$^2$ ............... C07D 501/36; A61K 31/545; C07D 501/60
[52] U.S. Cl. ...................... 424/246; 544/21; 544/26; 544/27
[58] Field of Search .................. 260/243 C; 424/246

[56] References Cited

U.S. PATENT DOCUMENTS

| 3,812,110 | 5/1974 | Lee et al. | 260/243 C |
| 3,966,717 | 6/1976 | Cook et al. | 260/243 C |
| 3,971,778 | 7/1976 | Cook et al. | 260/243 C |
| 3,974,153 | 8/1976 | Cook et al. | 260/243 C |

FOREIGN PATENT DOCUMENTS 6,916,151  4/1971  Netherlands ................ 260/243 C

OTHER PUBLICATIONS

Glaxo, Chemical Abstracts, (1974) vol. 81, Abstract 37,558m.
Ibid.
vol. 81, Abstract 169,551p, (1974).
Ibid.
vol. 83, Abst. 179,082s, (1975).
Ibid.
vol. 83: 43,354z (1975).
V. Morrison et al., Organic Chemistry, (1966), p. 707.

*Primary Examiner*—Nicholas S. Rizzo
*Assistant Examiner*—David E. Wheeler
*Attorney, Agent, or Firm*—William H. Edgerton

[57] ABSTRACT

New semisynthetic cephalosporins are described whose structures are characterized by having an α-oxyimino group in the 7-acetamido moiety and a sulfosubstituted tetrazolylthiomethyl group at position 3. The compounds are active antibacterial agents especially against Gram negative organisms.

18 Claims, No Drawings

DERIVATIVES OF 7-(2-SUBSTITUTED-2-HYDROX-YIMINOACETAMIDO)-3-(1-SUBSTITUTED TETRAZOL-5-YLTHIOMETHYL-3-CEPHEM-4-CARBOXYLIC ACID

This invention comprises a new series of cephalosporin compounds which have antibacterial activity and which are characterized by having structures combining an α-oxyiminoacetamido at the 7-position with a sulfo substituted tetrazole thiomethyl group at position 3.

These compounds have potent antibacterial activity against both Gram positive and Gram negative organisms especially upon parenteral administration. A further part of invention comprises methods and compositions for inducing antibacterial activity in infected subjects by internal administration of the new compounds.

Prior art patents (for example, German Pat. Nos. 2,223,375 and 2,204,060) describe a large number of oxyimino compounds among which are those having structures with an α-oxyiminoacetamido at position 7 of the cephalosporin nucleus and a tetrazole methylthio at 3 but with no sulfo containing tetrazoles.

The compounds of this invention are represented by the following structural formula:

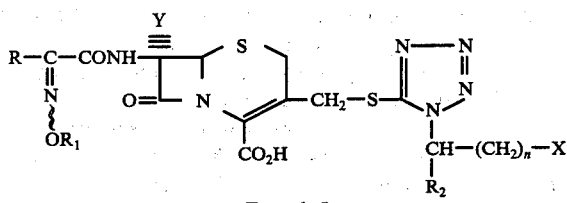

Formula I in which:

R is thienyl, furyl or phenyl optionally substituted as known in the cephalosporin art such as by hydroxy, halo such as bromo, chloro, or fluoro, nitro, ureido, methoxy, methylthio or trifluoromethyl on the phenyl ring or methyl or ethyl on the furyl or thienyl ring;

$R_1$ is hydrogen, lower alkyl such as from 1–6 carbon atoms, benzyl, phenethyl, thienylmethyl, or furylmethyl;

$R_2$ is hydrogen or methyl;

$n$ is an integer from 0–9;

X is sulfo (—$SO_3H$), sulfamyl (—$SO_2NH_2$), sulfamino (—$NHSO_3H$) or methylsulfonamido (—$NHSO_2CH_3$); and Y is hydrogen or methoxy.

A subgeneric group of compounds are the syn compounds of Formula I in which R is furyl, $R_1$ is hydrogen or methyl, Y is hydrogen or methoxy; $R_2$ is hydrogen; $n$ is 0–4 and X is sulfo, sulfamyl, sulfamino or methylsulfonamido. A more limited group are those in which X is sulfamino or methylsulfonamido. The sulfamyl congeners of Formula I may be optionally substituted with lower alkyl groups of 1–6 carbons such as methyl, ethyl, propyl, butyl etc. but with little additional advantage.

Also covered in this invention are the pharmaceutically acceptable, nontoxic derivatives of the compounds of Formula I: the salts, easily hydrolyzed esters of either a carboxy, sulfo or hydroxy function, hydrates or alcoholates. As examples of these one skilled in the art would be able to prepare and use the alkali metal salts such as the sodium or potassium salts, the alkaline metal salts such as the calcium salts, ammonium salts, organic amine salts such as those with procaine or dibenzylethylenediamine or the easily hydrolzed esters such as t-butyl, pivaloyloxymethyl, trichloroethyl, acetoxymethyl, benzyl, p-methoxybenzyl, glycyloxymethyl, indanyl or benzyloxymethyl. For other possible derivatives see those described in German Pat. No. 2,204,060.

The alkali metal salts are preferred especially the sodium or potassium salts with their hydrates. The compounds of Formula I of course exist as their syn (Z) or anti (E) isomers at the imino point of the structure. Alternatively they may be mixtures of isomers. The syn isomers are generally more active and are preferred. Normally the syn or anti configuration of the oximes is carried through the synthetic procedure from the substituted glyoxylic acid starting material. The heteroaryl groups at position 7 such as furyl or thienyl are either α or β attached preferably α. The phenyl substituents are preferably p-substituted.

The compounds of Formula I are prepared by N-acylation of an appropriate 7-amino-3-(sulfosubstituted tetrazole thiomethyl) cephalosporin nucleus of Formula II:

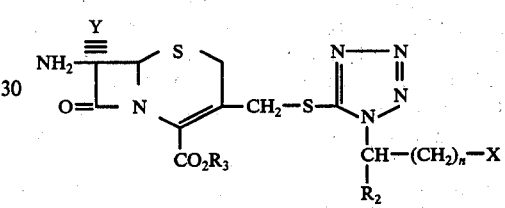

Formula II in which Y, $R_2$, $n$ are as defined for Formula I, X is sulfamyl or methyl sulfonamido and $R_3$ is hydrogen or the alcoholic portion of a carboxy protecting ester group, with an appropriate known α-aryl-α-oxyiminoacetic acid in its reactive acylating form such as acid chloride, mixed anhydride or activated ester. Alternatively a reagent such as dicyclohexylcarbodiimide or carbonyldiimidazole can be used with the acid providing the carboxylic groups at other sites are optionally protected with an easily removable protecting group as known to the art such as benzhydryl, t-butyl, trichloroethyl, benzyl, benzyloxymethyl, p-nitrophenyl, p-methoxyphenyl, p-nitrobenzyl esters. Also the hydroxy portion of the oxyimino acylating agent may be protected such as by the dichloroacetyl group (see German Pat. No. 2,204,060).

The 7-amino-3-sulfoalkyltetrazolythiomethyl cephalosporin starting materials of Formula II are prepared from reaction of 7-formamidocephalosporanic acid, prepared by reaction of the 7-aminocephalosporanic acid with formic acid and acetic anhydride, with a substituted tetrazole thiol of Formula III followed by treatment with acid such as hydrochloric acid to remove the formyl group.

Alternatively the compounds of Formula I are prepared by a displacement reaction at the 3-position of a known 7-(α-oxyiminoarylacetamido)cephalosporanic acid (see German Pat. No. 2,223,375) with the desired sulfosubstituted tetrazolethiol followed by removal of any protective group(s) present.

The sulfosubstituted tetrazole thiols mentioned above are the formula:

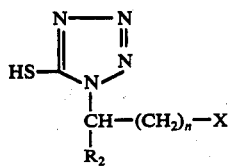

Formula III in which $R_2$, $n$ and X are as described above.

The protective groups used during these procedures can be removed according to methods well-known to the art such as with trifluoroacetic acid when a t-butyl protective group is used.

The acylating agents used as starting materials are either known or are prepared by known methods.

As stated above, the 7-amino-3-sulfosubstituted tetrazole thiomethyl cephalosporin starting materials of Formula II are made from the displacement reaction of a 7-aminocephalosporanic acid and a sulfosubstituted tetrazole thiol of Formula III.

The sulfosubstituted tetrazole thiols of Formula III where X is sulfo, lower alkyl or di(lower)alkylsulfamly are prepared by reaction of an N-alkyl dithiocarbamate, such as methyl 2-sulfoethyldithiocarbamate or methyl 3-(N-t-butylsulfamoylpropyl) dithiocarbamate or its corresponding sodium or potassium salt with an azide such as sodium azide. The N-alkyl dithiocarbamates are prepared by treatment of an aminoalkanesulfonic acid, for example 2-aminoethanesulfonic acid, or an amino(N-alkyl or N,N-dialkyl) sulfonamide such as 3-aminopropane-N-t-butylsulfonamide or its corresponding salt with carbon disulfide and an alkyl halide such as methyl iodide in the presence of a base such as sodium or potassium hydroxide.

The amino(N-alkyl or N,N-dialkyl)sulfonamides are prepared by reaction of an N-alkyl or N,N-dialkyl-phthalimidoalkylsulfonyl halide, preferably chloride, with an alkyl- or dialkylamine and then with hydrazine.

The phthalimidoalkysulfonyl halides are known or are prepared as described by Winterbottom et al., J. Amer. Chem. Soc. 69:1393 (1947) and Griffin and Hey, J. Chem. Soc., 3334 (1952).

When X is sulfamyl, the compounds of Formula II are prepared by removal of the N-alkyl group, which also serves as an amine protective group, from the corresponding N-alkylsulfamoylalkyltetrazole-5-thiol, preferably, a N-t-butylsulfamoylalkyltetrazole-5-thiol with for example anisole and trifluoroacetic acid.

The sulfaminoalkyltetrazole thiols of Formula III are prepared by reaction of the corresponding 1-aminoalkyl-5-(2,4-dinitrophenylthio)tetrazole compounds, prepared from 2,4-dinitrofluorobenzene and an 1-acetamidoalkyl-tetrazole-5-thiol followed by acid hydrolysis of the acetamido moiety, with sulfur trioxide-trimethylamine complex with subsequent cleavage of the 2,4-dinitrophenyl protecting group. The 1-acetamidoalkyltetrazole-5-thiols are prepared by reaction of an acetamidoalkyldithiocarbomate such as methyl 2-acetamidoethyldithiocarbamate with an azide such as sodium azide. The acetamidoalkyldithiocarbamates are prepared by treatment of an N-aminoalkylacetamide such as N-(2-aminoethyl)acetamide with carbon disulfide and an alkyl halide such as methyl iodide in the presence of a base such as triethylamine.

The methylsulfonamidoalkyltetrazole thiols are prepared by reacting the 1-aminoalkyl-5-(2,4-dinitrophenylthio)tetrazole intermediates with mesyl chloride in pyridine followed by removal of the protective group with 5% sodium methoxide in methanol.

As stated above, the compounds of this invention are very potent antibacterial agents against Gram negative and Gram positive organisms. They are especially active against Gram negative organisms. The furyl congeners are particularly active.

Table 1 contains minimum inhibitory concentrations in μg./ml. of a number of representative compounds compared with standard agents.

TABLE 1

MIC (μg/ml) in vitro

| | G+ S. Aureus HH 127 | G+ S. Aureus SK 23390 | G+ S. villaluz SK 70390 | G+ Strep. Faecalis HH 34358 | G− E. coli SK 12140 | G− E. coli HH 33779 | G− Kleb. pneumoniae SK 4200 | G− Kleb. pneumoniae SK 1200 | G− Salmonella ATCC 12176 | G− Pseudo Aeruginosa HH 63 | G− Serratia Marcescens ATCC 13880 | G− Proteus morgani 179 | G− Entero. aerogenes ATCC 13048 | G− Entero. cloacae HH 31254 | G− P. Mirabilis PM 444 |
|---|---|---|---|---|---|---|---|---|---|---|---|---|---|---|---|
| A | 3.1 | 3.1 | >200 | 100 | 0.8 | 1.6 | 0.8 | 0.4 | 0.4 | 100 | 3.1 | 1.6 | 3.1 | 0.8 | 1.6 |
| A | 3.1 | 3.1 | >200 | 200 | 0.8 | 1.6 | 0.8 | 0.4 | 0.8 | 100 | 6.3 | 1.6 | 3.1 | 0.8 | 0.2 |
| B | 1.6 | 1.6 | >200 | 25 | 6.3 | 6.3 | 3.1 | 3.1 | 1.6 | 200 | 12.5 | 6.3 | 12.5 | 3.1 |  |
| C | 0.8 | 0.8 | 100 | 6.3 | 1.6 | 3.1 | 1.6 | 0.8 | 0.8 | >200 | 12.5 | 25 | 6.3 | 1.6 |  |
| Cefazolin | 0.4 | 0.2 | 200 |  | 0.8 | 1.6 | 1.6 | 0.4 | 0.8 | >200 | >200 | 200 | 1.6 | 0.8 | 3.1 |
| Cefoxitin | 1.6 | 3.1 | 100 | 200 | 6.3 | 12.5 | 6.3 | 3.1 | 3.1 | >200 | 12.5 | 12.5 | 25 | 6.3 | 6.3 |
| Cefurox-ime | 0.8 | 1.6 | >200 | 12.5 | 6.3 | 6.3 | 6.3 | 3.1 | 3.1 | >200 | 12.5 | 50 | 6.3 | 3.1 | 1.6 |

A is 7β-(syn-2-methoxyimino-2-α-furylacetamido)-3-(1-sulfomethyltetrazol-5-ylthiomethyl)-3-cephem-4-carboxylic acid disodium salt hydrate.

B is 7β-(syn-2-methoxyimino-2-phenylacetamido)-3-(1-sulfomethyltetrazol-5-ylthiomethyl)-3-cephem-4-carboxylic acid disodium salt.

C is 7β-(syn-2-hydroxyimino-2-phenylacetamido)-3-(1-sulfomethyltetrazol-5-ylthiomethyl)-3-cephem-4-carboxylic acid disodium salt. In the standard in vivo mouse protection test Compound C had an $ED_{50}$ (s.c.) of 4.4 mg./kg. against Kleb. pneumo. 4200; 25 mg./kg. against E. coli 12140; Compound B 45 mg./kg. against Kleb. and 43, >50 against E. coli.

The following preparations of starting materials and end products are designed to make the synthesis and use of these new compounds apparent to those skilled in the art.

EXAMPLE 1

To a solution of 20.4 g. (0.20 mol) of N-(2-aminoethyl) acetamide in 200 ml. of 95% ethanol was added 27.9 ml. (0.20 mol) of triethylamine and 12.0 ml. (0.20 mol) of carbon disulfide. The exothermic reaction reached reflux and the cooled to ambient temperature over a 1.5 hour period. Methyl iodide (28.4 g; 0.20 ml.) was added which again produced an exothermic reaction. After 1.75 hours the reaction mixture was evaporated to dryness and the solid residue was dissolved in 200 ml. of water. The aqueous solution was extracted twice with 250 ml. portions of ethyl acetate. The extracts were combined, shaken with sodium thiosulfate, dried ($MgSO_4$) and evaporated to dryness to give methyl 2-acetamidoethyldithiocarbamate.

To a solution of 38.4 g. (0.198 mol) of methyl 2-acetamidoethyldithiocarbamate in 100 ml. of 95% ethanol was added a solution of 13.5 g (0.208 mol) of sodium azide in 100 ml. of water. The reaction mixture was refluxed for 24 hours then cooled and concentrated under reduced pressure to about half volume. The solution was cooled to 15° and 50 ml. of 6N sulfuric acid was added. The acidic solution was filtered and the filtrate was concentrated to about 100 ml. and chilled at 5° C. to induce crystallization of 1-(2-acetamidoethyl)-tetrazole-5-thiol which was collected by filtration, mp 139°-139.5° C. Additional amounts of the product were obtained by continuous extraction of the filtrate with ethyl acetate.

A solution of 9.3 g. (0.050 mol) of 2,4-dinitrofluorobenzene in 50 ml. of acetone was added to a solution of 9.35 g. (0.050 mol) of 1-(2-acetamidoethyl)tetrazole-5-thiol and 6.85 ml. (0.050 mol) of triethylamine in 100 ml. of acetone and the reaction mixture was stirred for 1 hour. The solid material was collected by filtration and recrystallized from acetonitrile to give 1-(2-acetamidoethyl)-5-(2,4-dinitrophenylthio)tetrazole, mp 197°-198° C.

A mixture of 6.5 g. (0.02 mol) of 1-(2-acetamidoethyl)-5-(2,4-dinitrophenylthio)tetrazole, 100 ml. of 12 N hydrochloric acid and 100 ml. of 95% ethanol was refluxed for 4.5 hours. The mixture was evaporated to dryness to give a gummy residue which crystallized upon addition of ethanol to give 1-(2-aminoethyl)-5-(2,4-dinitrophenylthio)-tetrazole hydrochloride, mp 217°-219° C. (d).

To a solution of 3.5 g. (0.01 mol) of 1-(2-aminoethyl)-5-(2,4-dinitrophenylthio)tetrazole hydrochloride in 30 ml. of dry dimethylformamide was added 1.4 g. (0.01 mol) of sulfur trioxide-trimethylamine complex followed by 1.4 ml. (0.01 mol) of triethylamine. The mixture was stirred for 0.5 hour and then filtered. The filtrate was evaporated in vacuo, acetone was added to the residue, the precipitate was removed by filtration and the filtrate was evaporated to dryness. Methanol was added to the residue, and the solid material produced upon scratching was removed by filtration. The methanolic filtrate was brought to pH 11.3 by addition of 5% methanolic sodium methoxide, stirred for 1.25 hours, filtered and diluted with 300 ml. of ether. The resulting solid was removed by filtration and the filtrate was evaporated to dryness to give a residue which was triturated with 95% ethanol to induce crystallization. The solid product was collected by filtration and dissolved in methanol and the methanolic solution was concentrated to 10 ml., diluted with 75 ml. of 95% ethanol and re-concentrated to 5 ml. to give 1-(2-sulfaminoethyl)tetrazole-5-thiol disodium salt, mp 122°-127° C.

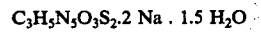

$C_3H_5N_5O_3S_2 \cdot 2$ Na $\cdot 1.5 H_2O$

Calculated: 12.16% C; 2.72% H; 23.64% N; Found: 12.25% C; 2.98% H; 23.77% N.

A solution of 1-(2-sulfaminoethyl)tetrazole-5-thiol disodium salt in water is passed through a polystyrene type sulfonic acid ion exchange resin (Amberlite IR-120H) to give, after lyophilization, 1-(2-sulfaminoethyl)tetrazole-5-thiol.

A solution of 7-[syn-2-methoxyimino-2-furylacetamido]cephalosporanic acid (3.05 g, 7.2 mmol) and 1-sulfaminoethyltetrazole-5-thiol disodium salt (1.94 g, 7.2 mmol) in 50 ml. of water containing sodium bicarbonate (0.61 g, 7.2 mmol) is heated at 65°-70° C. for several hours while maintaining the pH of the reaction mixture at 7.4-7.6 with dilute bicarbonate. After cooling to room temperature the reaction mixture is extracted with ethyl acetate (discarded), the aqueous phase adjusted to pH 2.0 with dilute hydrochloric acid and extracted with ethyl acetate. The acidic aqueous layer is neutralized to pH 7.0 with dilute bicarbonate and chromatographed over a crosslinked copolymer of styrene-divinylbenzene (XAD-4 Rohm and Haas Co. Philadelphia, Pa.). Elution with aqueous methanol and lyophilization of these fractions shown to contain product by thin layer chromatography gives 7-[syn-2-methoxyimino-2-α-furylacetamido]-3-[1-(2-sulfaminoethyl)tetrazol-5-ylthiomethyl]-3-cephem-4-carboxylic acid, disodium salt.

EXAMPLE 2

A solution of 7-syn-[2-methoxyimino-2-phenylacetamido]cephalosporanic acid (5.42 g, 0.013 mol) and 1-sulfaminoethyltetrazol-5-thiol disodium salt (3.5 g, 0.013 mol) in 100 ml. of water containing sodium bicarbonate (1.1 g, 0.013 mol) is heated at 65°-70° C. for several hours while maintaining the pH at 7.4-7.6 with dilute bicarbonate. After cooling to room temperature the reaction mixture is extracted with ethyl acetate (discarded), the aqueous phase adjusted to pH 2.0 with dilute hydrochloric acid and extracted with ethyl acetate. The acidic aqueous layer is neutralized to pH 7.0 with dilute $NaHCO_3$ and chromatographed on XAD-4 resin. Elution with aqueous methanol followed by lyophilization of the eluates affords 7-[syn-2-methoxyimino-2-phenylacetamido]-3-[1-(2-sulfaminoethyl)tetrazol-5-ylthiomethyl]-3-cephem-4-carboxylic acid, disodium salt.

EXAMPLE 3

When an equivalent amount of an N-aminoalkylacetamide listed below:

N-(3-aminopropyl)acetamide
N-(4-aminobutyl)acetamide
N-(5-aminopentyl)acetamide is used in the procedure of Example 1 in place of N-(2-aminoethyl)-acetamide and the resulting dithiocarbamates are treated with sodium azide to produce the corresponding 1-acetamidoalkyltetrazole-5-thiols which are converted to the 1-sulfaminoalkyl derivatives, all as described therein, the following 1-sulfaminoalkyltetrazole-5-thiols are obtained:

1-(3-sulfaminopropyl)tetrazole-5-thiol
1-(4-sulfaminobutyl)tetrazole-5-thiol
1-(5-sulfaminopentyl)tetrazole-5-thiol.

Reaction of the disodium salt of a 1-sulfaminoalkyltetrazole-5-thiol listed above with 7-[syn-2-methoxyimino-2-α-furylacetamido]cephalosporanic acid sodium salt as described in the procedure of Example 1 followed by conversion of the salt formed to the free acids, gives the following compounds of this invention:

7-[syn-2-methoxyimino-2-α-furylacetamido]-3-[1-(3-sulfaminopropyl)tetrazol-5-ylthiomethyl]-3-cephem-4-carboxylic acid 7-[syn-2-methoxyimino-2-α-furylacetamido]-3-[1-(4-sulfaminobutyl)tetrazol-5-ylthiomethyl]-3-cephem-4-carboxylic acid 7-[syn-2-methoxyimino-2-α-furylacetamido]-3-[1-(5-sulfaminopentyl)tetrazol-5-ylthiomethyl]-3-cephem-4 carboxylic acid.

EXAMPLE 4

Reaction of a cephalosporanic acid listed below or its corresponding salt:

7-[syn-2-ethoxyimino-2-(thien-2-yl)acetamido]cephalosporanic acid

7-[syn-2-benzyloxyimino-2-(fur-2-yl)acetamido]cephalosporanic acid or

7-[syn-2-tert-butoxyimino-2-(fur-2-yl)acetamidol]-cephalosporanic acid with 1-(2-sulfaminoethyl)tetrazole-5-thiol disodium salt by procedures described hereinabove gives, after conversion of the product to the free acid, the following compounds of this invention:

7-[syn-2-ethoxyimino-2-(thien-2-yl)acetamido]-3-[1-(2-sulfaminoethyl)tetrazol-5-ylthiomethyl]-3-cephem-4-carboxylic acid 7-[syn-2-benzyloxyimino-2-(fur-2-yl)acetamido]-3-[1-(2-sulfaminoethyl)tetrazol-5-ylthiomethyl]-3-cephem-4-carboxylic acid or 7-[syn-2-tert-butoxyimino-2-(fur-2-yl)acetamido]-[1-(2-sulfaminoethyl)tetrazol-5-ylthiomethyl]-3-cephem-4-carboxylic acid.

EXAMPLE 5

To a mixture of 97 g. (200 ml, 2.1 mol) of formic acid, distilled from anhydrous copper sulfate, and 37.5 ml. (0.4 mol) of acetic anhydride was added 25.0 g. (0.1 mol) of 7-aminocephalosporanic acid. The mixture was stirred at ambient temperature for 0.5 hour, then evaporated to dryness. The residue was dissolved in ethyl acetate and the ethyl acetate solution was filtered and evaporated to dryness to give a residue which was recrystallized from ether-petroleum ether to give 7-formamidocephalosporanic acid.

A mixture of 1.0 g. (3.3 mmol) of 7-formamidocephalosporanic acid and 0.7 g. (2.6 mmol) of 1-(2-sulfaminoethyl)tetrazole-5-thiol disodium salt in 15 ml. of water is stirred at 65°-70° for 3 hours while maintaining the pH at 7.0. The mixture is cooled, acidified to pH 1.0 with hydrochloric acid and extracted with ethyl acetate. The extract is filtered and the filtrate is evaporated to dryness to give a residue which is dissolved in methanol. The methanol solution is filtered and ether is added to precipitate the intermediate compound which is collected by filtration; 7-amino-3-[1-(2-sulfaminoethyl)tetrazol-5-ylthiomethyl]-3-cephem-4-carboxylic acid.

Syn-then-2-yloxyimino-(thien-2-yl)acetyl chloride (2.8 mmol) is dropwise added to a mixture of 1.0 g. of 7-amino-3-[1-(2-sulfaminoethyl)tetrazol-5-ylthiomethyl]-3-cephem-4-carboxylic acid and 0.9 g. (9.0 mmol) of triethylamine in 10 ml. of dry dimethylformamide. The reaction mixture is stirred for 1.5 hour at −10° C., then it is warmed to ambient temperature and stirred for 1 hour. This mixture is filtered and the filtrate is diluted with 200 ml. of ether-petroleum ether. The precipitate is collected by filtration and dissolved in methanol. The methanol solution is filtered and the filtrate is evaporated to dryness to give 7-[syn-then-2-yloxyimino-(thien-2-yl)acetamido]-3-[1-(2-sulfaminoethyl)tetrazol-5-ylthiomethyl]-3-cephem-4-carboxylic acid.

EXAMPLE 6

A mixture of 4.9 g. (0.0141 mol) of 1-(2-aminoethyl)-5-(2,4-dinitrophenylthio)tetrazole hydrochloride and 100 ml. of pyridine is reacted with 1.5 ml. of mesyl chloride. After 1.5 hours, added 0.5 ml. of mesyl chloride. After another hour, the reaction mixture stripped. Residue was taken up in dimethyl formamide. Diluted with water to give the N-mesylated product.

A mixture of 4.46 g. (0.0115 mol) of the mesyl compound in 60 ml. of 5% sodium methoxide/methanol. After ½ hour, the mixture was concentrated in vacuo. The pH was taken to 1.4 with 3N hydrochloric acid. The mixture was extracted with ethylacetate. The residue from the dried extracts gives the desired 1-(2-methanesulfonamidoethyl)tetrazole-5-thiol.

To a suspension of 7-aminocephalosporanic acid (14.1 g., 0.05 mol) in 250 ml. of water and 250 ml. of acetone is added a solution of sodium bicarbonate (10.5 g., 0.125 mol) in 250 ml. of water. This solution is heated to 45° C. and a solution of 1-(2-methanesulfonamidoethyl)tetrazol-5-thiol (16.7 g., 0.075 mol) in 250 ml. of acetone is added. The mixture is heated under reflux while maintaining the pH at 7.6-7.8 by the addition of dilute bicarbonate as necessary. Progress of the reaction is followed by observing the disappearance of the acetoxy peak in the infrared spectrum of a solid sample isolated from an aliquot portion of the reaction mixture. When reaction is complete the solution is cooled in an ice bath and acidified to pH 3.5 with dilute hydrochloric acid. The precipitate is collected, washed with water, acetone and then dried to give 7-amino-3-[1-(2-methanesulfonamidoethyl)tetrazol-5-ylthiomethyl]-3-cephem-4-carboxylic acid.

A solution of syn-2-methoxyimino-2-furylacetyl chloride (1.4 g., 7.5 mmol) in 50 ml. of acetone is added gradually to a cold (−10°) stirred solution of 7-amino-3-[1-(2-methanesulfonamidoethyl)tetrazol-5-ylthiomethyl]-3-cephem-4-carboxylic acid (2.6 g., 6 mmol) in 100 ml. of water and 100 ml. of acetone containing (1.65 g., 19.5 mmol) of bicarbonate. After stirring for 30 minutes at −10° C. and 1.5 hr. at ambient temperature the acetone is evaporated and the aqueous residue is extracted with ethyl acetate (discarded). The aqueous layer is adjusted to pH 2.0 with dilute HCl and extracted with ethyl acetate. Evaporation of the combined, dried (MgSO$_4$) extracts affords 7-[syn-2-methoxyimino-2-α-furylacetamido]-3-[1-(2-methanesulfonamidoethyl)tetrazol-5-ylthiomethyl]-3-cephem-4-carboxylic acid.

The methylsulfonamido compound is converted to the potassium salt using potassium methoxide/methanol. The crude salt (1.5 mmol) in dry dimethylformamide is mixed with 1.65 mmol. of bromomethylacetate in dimethylformamide at ice bath temperature. After ½ hour stirring the mixture is allowed to warm to room temperature then quenched with water. The desired ester is isolated by extraction into methylene chloride. Substituting iodomethyl pivalate gives the pivaloyloxymethyl ester at position-4. These and other lower alkanoyloxy methyl esters or the indanyl ester are used as suspension for injection or as oral products. If an acid group is present at 3 a second ester may be formed here.

EXAMPLE 7

To a solution of 112 g. (2.0 mol) of potassium hydroxide and 111 g. (1.0 mol) of aminomethanesulfonic acid in 250 ml. of water at 25° C. was added 71 ml. of carbon disulfide. The reaction mixture was stirred for 12 hours and 250 ml. of ethanol was added. The reaction vessel was fitted with a reflux condenser and 62 ml. (1.0 mol.) of methyl iodide was added. When the exothermic reaction cooled to ambient temperature the solid product was collected by filtration. The solid was extracted with hot methanol and the extract was concentrated to give methyl sulfomethyldithiocarbamate as the potassium salt.

A mixture of 45.3 g. (0.19 mol) of methyl sulfomethyldithiocarbamate potassium salt and 16.9 g. (0.26 mol) of sodium azide in 425 ml. of water was heated at 80° C. for 4.75 hours. The reaction mixture was passed through an Amberlite IR-120H ion exchange resin column and eluted with water until the pH of the eluant became 3.5. The eluant was extracted with ether and the aqueous solution was evaporated to dryness to give 1-sulfomethyltetrazole-5-thiol. The disodium salt is prepared using sodium methoxide-methanol in isopropanol. 1-Sulfomethyltetrazole-5-thiol sodium salt was precipiated and was collected by filtration.

A solution of 7-(2-hydroxyimino-2-phenylacetamido)cephalosporanic acid (5.25 g., 0.013 mol) and 1-sulfomethyltetrazol-5-thiol disodium salt (2.4 g., 0.01 mol) in 75 ml. of water containing sodium bicarbonate (1.25 g., 0.015 mol) was heated at 68° C. for 4.5 hr. After 1.5 hr. an additional 1.0 g. of 7-(2-hydroxyimino-2-phenylacetamido)cephalosporanic acid was added. The pH throughout was maintained at 7.4–7.6 by periodic addition of dilute NaHCO$_3$ solution. After cooling to room temperature the reaction mixture was extracted with ethyl acetate, the aqueous layer acidified to pH 2.0 with dilute hydrochloric acid and extracted with ethyl acetate. The acidic aqueous layer was neutralized to pH 7.0 with dilute bicarbonate and chromatographed on XAD-4 resin. Elution with 80% aqueous methanol gave 1.4 g. of 7-(syn-2-hydroxyimino-2-phenylacetamido)-3-(1-sulfomethyltetrazol-5-ylthiomethyl)-3-cephem-4-carboxylic acid, disodium salt.

$C_{18}H_{15}Na_2N_7O_8S_3 \cdot 1.5 H_2O$

Calculated: C, 35.00; H, 3.19; N, 14.90; Found: C, 34.50; H, 2.89; N, 15.64.

The anti isomer is prepared starting with the 7-(anti-2-hydroxyimino-2-phenylacetamido)cephalosporanic acid as starting material. Also the α-furyl congener is prepared by substituting an equimolar quantity of 7-(syn-2-hydroxyimino-2-α-furylacetamido)cephalosporanic acid. These substituted cephalosporanic acid are prepared as described in German Pat. No. 2,223,375.

EXAMPLE 8

A solution of 7-[syn-2-methoxyimino-2-phenylacetamido]cephalosporanic acid (5.42 g., 0.013 mol) and 1-sulfomethyltetrazol-5-thiol disodium salt (2.4 g., 0.01 mol) in 75 ml. of water containing sodium bicarbonate (1.25 g., 0.015 mol) was heated at 68° C. for 4.5 hr. while maintaining the pH at 7.4–7.6 by periodic addition of dilute bicarbonate solution. The mixture was cooled to room temperature and extracted with ethyl acetate. The aqueous layer was separated, acidified to pH 2.0 with dilute hydrochloric acid and extracted with ethyl acetate. The acidic aqueous layer was neutralized to pH 7.0 with dilute bicarbonate and applied to a column of XAD-4 resin. Elution with 80% aqueous methanol followed by lyophilization gave 1.26 g. of 7-[syn-2-methoxyimino-2-phenylacetamido]-3-(1-sulfomethyltetrazol-5-ylthiomethyl)-3-cephem-4-carboxylic, disodium salt.

$C_{19}H_{17}Na_2N_7O_8S_3 \cdot H_2O \cdot 0.20CH_3OH$

Calculated: C, 36.14; H, 3.12; N, 15.36; Found: C, 36.60; H, 3.57; N, 14.74.

EXAMPLE 9

A solution of 7-[syn-2-methoxyimino-2-furylacetamido]cephalosporanic acid (3.05 g., 7.2 mmol) and 1-sulfomethyltetrazol-5-thiol disodium salt (1.73 g., 7.2 mmol) in 50 ml. of water containing sodium bicarbonate (0.61 g., 7.2 mmol) was heated at 68° C. for 6 hours while maintaining the pH at 7.4–7.6 with dilute bicarbonate. The cooled reaction mixture was extracted with ethyl acetate, the aqueous phase adjusted to pH 2.0 with dilute hydrochloric acid and extracted with ethyl acetate. The acidic aqueous layer was adjusted to pH 7.0 with dilute bicarbonate and chromatographed on XAD-4 resin. Elution with 50% aqueous methanol followed by lyophilization afforded 0.9 g. of 7-[syn-2-methoxyimino-2-furylacetamido]-3-(1-sulfomethyltetrazol-5-ylthiomethyl)-3-cephem-4-carboxylic acid, disodium salt.

$C_{17}H_{15}Na_2N_7O_8S_3 \cdot H_2O$

Calculated: C, 32.64; H, 2.73; N, 15.67; Found: C, 32.79; H, 2.96; N, 14.67.

EXAMPLE 10

A cold solution of 7β-amino-7α-methoxycephalosporanic acid benzhydryl ester (5.25 g., 0.012 mol) in 200 ml. of methylene chloride containing N,N-diethylaniline (1.79 g., 0.012 mol) is treated dropwise over 20 minutes with a solution of syn-2-methoxyimino-2-furylacetyl chloride (2.24 g., 0.012 mol) in 50 ml. of methylene chloride. After stirring for 30 minutes the mixture is extracted successively with 5% sodium bicarbonate, 5% hydrochloric acid and finally with brine. The organic phase is dried (MgSO$_4$) and the solvent evaporated to give 7α-methoxy-7β-[syn-2-methoxyimino-2-furylacetamido]-cephalosporanic acid benzhydryl ester. The ester is dissolved in cold trifluoroacetic acid anisole (2:1) and stirred at ambient temperature for 1.5 hr. The solvent is evaporated, the residue dissolved in ethyl acetate, washed with water, dried and diluted with petroleum ether to give 7α-methoxy-7β-[syn-2-methoxyimino-2-furylacetamido]-cephalosporanic acid.

The above cephalosporanic acid (2.1 g., 5 mmol) is suspended in 75 ml. of H$_2$O and solid sodium bicarbonate is added until solution is complete. To this solution is added 1-sulfomethyltetrazole-5-thiol disodium salt (1.8 g., 7.5 mmol) and the mixture heated at 70° C. for several hours. The pH of the reaction mixture is maintained at 7.5 by periodic addition of 3N hydrochloric acid. When t.l.c. indicated disappearance of starting material the reaction is cooled and the aqueous solution is chromatographed on XAD-4 resin. Elution with methanol and evaporation of the solvent gives 7α-methoxy-7β-[syn-2-methoxyimino-2-α-furylacetamido]-3-(1-sulfomethyltetrazol-5-ylthiomethyl)-3-cephem-4-carboxylic acid, disodium salt.

EXAMPLE 11

To a suspension of 7α-methoxy-6β-[syn-2-methoxyimino-2-furylacetamido]cephalosporanic acid (4.2 g., 0.01 mol) in 150 ml. of water is added solid sodium bicarbonate until solution is complete. Then 1-(2-sulfoaminoethyl)-tetrazole-5-thiol, disodium salt (4.05 g., 0.015 mol) is added and the mixture heated to 70° C. for several hours. The pH of the reaction mixture is maintained at 7.4–7.6 by addition of 3N hydrochloric acid or dilute bicarbonate as necessary. When t.l.c. indicates that the reaction is complete the solution is cooled to room temperature and chromatographed on XAD-4 resin. Elution with methanol and evaporation of the solvent gives 7α-methoxy-7β-[syn-2-methoxyimino-2-α-furylacetamido]-3-[1-(2-sulfaminoethyl) tetrazol-5-ylthiomethyl]-3-cephem-4-carboxylic acid, disodium salt.

EXAMPLE 12

A solution of 2.73 g. (0.01 mol) of 2-phthalimidoethanesulfonyl chloride in 20 ml. of chloroform was added dropwise to a solution of 2.19 g. (0.03 mol.) of t-butylamine in 20 ml. of chloroform at 5°. The reaction mixture was warmed to ambient temperature and stirred for three hours. The precipitate was removed by filtration and the filtrate was evaporated to dryness to give a residue which was purified by chromatography on silica with 19:1 chloroform-methanol as eluant to give 2-N-t-butylphthalimidoethanesulfonamide. 2-N-t-Butylphthalimidoethanesulfonamide (2.10 g., 6.78 mmol.) was suspended in 20 ml. of ethanol and 0.344 g. of hydrazine hydrate was added. The reaction mixture was refluxed for three hours, then evaporated to dryness. The residue was suspended in 45 ml. of water and acidified to pH 3.0 by addition of dilute hydrochloric acid. The acid solution was filtered and the filtrate evaporated to dryness to give 2-aminoethane-N-t-butylsulfonamide hydrochloride.

2-Aminoethane-N-t-butylsulfonamide hydrochloride (1.25 g., 5.78 mmol). was added to a solution of 1.17 g. (11.56 mmol.) of triethylamine in 20 ml. of ethanol. Carbon disulfide (0.44 g., 5.78 mmol.) was added, the mixture was stirred at 25° for 1.5 hours, then 0.82 g. (5.78 mmol.) of methyl iodide in 5 ml. of ethanol was added and the resulting mixture was stirred for 1.5 hours. The mixture was evaporated to dryness and the residue was dissolved in water and acidified to pH 2.0 with dilute hydrochloric acid. The aqueous mixture was extracted with ethyl acetate and the extract was dried (MgSO$_4$) and evaporated to dryness to give methyl 2-(N-t-butylsulfamyl)ethyldithiocarbamate.

Methyl-2-(N-t-butylsulfamyl)ethyldithiocarbamate was treated with sodium azide as described in the procedure of Example 1 for 35 minutes to give 1-(2-N-t-butylsulfamylethyl)tetrazole-5-thiol.

1-(2-N-t-Butylsulfamylethyl)tetrazole-5-thiol (1.0 g.) was suspended in 10 ml. of anisole and 20 ml. of trifluoroacetic acid is added. The solution was heated at 56° for 3.5 hours, then cooled. The precipitate was collected by filtration and washed with petroleum ether to give 1-(2-sulfamylethyl)tetrazole-5-thiol.

A solution of 0.210 g. (2.5 mmol.) of sodium bicarbonate in 5 ml. of water was added to a suspension of 0.272 g. (1 mmol.) of 7-aminocephalosporanic acid in 5 ml. of water and 2.5 ml. of acetone at 15°. The solution was heated to 45°, a solution of 0.314 g. (1.5 mmol.) of 1-(2-sulfamylethyl)tetrazole-5-thiol) in 10 ml. of acetone was added and the reaction mixture was refluxed for two hours while maintaining the pH at 7.4–7.6 by addition of aqueous sodium bicarbonate solution. The mixture was cooled and acidified to pH 4.0 with dilute hydrochloric acid. The precipitate was collected by filtration to give 7-amino-3-[1-(2-sulfamylethyl)tetrazol-5-ylthiomethyl]-3-cephem-4-carboxylic acid.

A solution of syn-2-methoxyimino-2-furylacetyl chloride (2.8 g., 0.015 mol) in 100 ml. of acetone is added gradually to a cold (−10°) stirred solution of 7-amino-3[1-(2-sulfamylethyl) tetrazol-5-ylthiomethyl]-3-cephem-4-carboxylic acid (5.1 g., 0.012 mol.) in 200 ml. of water and 200 ml. of acetone containing sodium bicarbonate (3.3 g., 0.039 mol.). After stirring for 30 minutes at −10° C. and 1.5 hr at ambient temperature the acetone is evaporated and the aqueous residue is extracted with ethyl acetate (discarded). The aqueous layer is adjusted to pH 2.0 with dilute hydrochloric acid and extracted with ethyl acetate. Evaporation of the combined, dried (MgSO$_4$) organic extracts gives 7-[syn-2-methoxyimino-2-furylacetamido]-3-[1-(2-sulfamylethyl)tetrazol-5-ylthiomethyl]-3-cephem-4-carboxylic acid. The compound is purified by chromatography on silica gel and elution with chloroformmethanol-formic acid (90:10:1).

EXAMPLE 13

When an equivalent amount of 1-(2-N-t-butylsulfamoylethyl)tetrazole-5-thiol is reacted with 7-aminocephalosporanic acid as described in Example 12, 7-amino-3-[1-(2-N-t-butylsulfamylethyl)tetrazol-5-ylthiomethyl]-3-cephem-4-carboxylic acid is obtained.

Acylation as in Example 12 with anti-2-methoxyimino-2-phenylacetyl chloride gives 7-[anti-2-methoxyimino-2-phenylacetamido]-3-[1-(2-N-t-butylsulfamylethyl)tetrazol-5-ylthiomethyl]-3-cephem-4-carboxylic acid.

EXAMPLE 14

2-Aminoethanesulfonic acid (50 g., 0.4 mol.) was added to a solution of 45 g. (0.8 mol.) of potassium hydroxide in 100 ml. of water at 25°. Carbon disulfide (24.4 ml., 0.4 mol.) was added and the reaction mixture was refluxed for 2.5 hours. Ethanol was added to the warm solution, the mixture was cooled to ambient temperature, 57 g. (0.4 mol.) of methyl iodide was added and the resulting mixture was stirred for 1.5 hours. The mixture was evaporated in vacuo and the residue recrystallized from hot ethanol containing 3% water to give methyl 2-sulfoethyldithiocarbamate potassium salt.

A mixture of 21.5 g. (0.087 mol.) of methyl 2-sulfoethyldithiocarbamate potassium salt (0.5 hydrate) and 7.16 g. (0.11 mol.) of sodium azide in 200 ml. of water was refluxed for two hours. The solution was cooled to 25° and extracted with ethyl acetate. The aqueous phase was treated with Amberlite IR-120H resin, washed with ether and evaporated to give an oil. The oil was dissolved in acetone, the solution was filtered and the filtrate was evaporated to dryness to give 1-(2-sulfoethyl)-tetrazole-5-thiol. The thiol was dissolved in isopropanol, cyclohexylamine was added until pH 8–9 and acetonitrile was added to give 1-(2-sulfoethyl)tetrazole-5-thiol as the di-cyclohexylamine salt.

1-(2-Sulfoethyl)tetrazole-5-thiol di-cyclohexylamine salt was dissolved in water and treated with Amberlite IR-120H resin to give 1-(2-sulfoethyl)tetrazole-5-thiol.

To a solution of 2.1 g. (0.01 mol.) of 1-(2-sulfoethyl)tetrazole-5-thiol in 100 ml. of water is added to 0.015 mol. of 7-[syn-2-furylmethoxyimino-2-α-furylacetamido]cephalosporanic acid sodium salt and 1.68 g. (0.02 mol.) of sodium bicarbonate. The mixture was stirred at 70° for 2.5 hours then cooled and acidified to pH 1.8 with 3N hydrochloric acid. The acid solution was extracted with ethyl acetate and ether, acidified to pH 0.9 and chromatographed on a XAD-8 resin column with water as eluant to give the 7-[syn-2-α-furylmethoxyimino-2-α-furylacetamido]-3-[1-(2-sulfoethyl)tetrazol-5-ylthiomethyl]-3-cephem-4-carboxylic acid.

The title compound was converted to the corresponding disodium salt by treatment with sodium methoxide.

EXAMPLE 15

A suspension of 15.1 g. (0.136 mol.) of aminomethanesulfonic acid and 14.2 g. (0.145 mol.) of anhydrous potassium acetate in 48 ml. of acetic acid is refluxed for ten minutes. Phthalic anhydride (21.4 g., 0.145 mol.) is then added and the resulting mixture is refluxed for 2.5 hours. The product is collected by filtration and washed with acetic acid and ethanol to give phthalimidomethanesulfonic acid potassium salt.

To 41.7 g. (0.15 mol.) of phthalimidomethanesulfonic acid potassium salt in 220 ml. of dry benzene is added 22.5 g. (0.132 mol.) of phosphorus pentachloride. The reaction mixture is refluxed on a steam bath for one hour, then an additional 22.5 of phosphorus pentachloride is added and heating is continued for 1.5 hours. The reaction mixture is evaporated to dryness, crushed ice is added to the residue and the slurry is filtered. The product is washed with water to give phthalimidomethanesulfonyl chloride.

When phthalimidomethanesulfonyl chloride is substituted in the procedure of Example 12 for 2-phthalmimidoethanesulfonyl chloride, N-t-butylphthalimidomethanesulfonamide is prepared which is converted to 1-N-t-butylsulfamoylmethyltetrazole-5-thiol as described therein. Treatment of 1-N-t-butylsulfamoylmethyltetrazole-5-thio with trifluoroacetic acid as described gives 1-sulfamoylmethyltetrazole-5-thiol.

Reaction of 1-sulfamoylmethyltetrazole-5-thiol with 7-aminocephalosporanic acid and treatment of the product 7-amino-3-(1-sulfamoylmethyltetrazol-5-ylthiomethyl)-3-cephem-4-carboxylic acid with any acid chloride described herein give the sulfamoylmethyltetrazole derivative.

EXAMPLE 16

A suspension of 56 g. (1.0 mol.) of potassium hydroxide and 118.7 g. (0.5 mol.) of 10-aminodecanesulfonic acid in 170 ml. of water is stirred for 30 minutes at 25°, then 40 g. (0.52 mol.) of carbon disulfide and 80 ml. of ethanol are added and the reaction mixture is stirred at 25° for 12 hours. The mixture is refluxed gently for two hours and cooled. Methyl iodide (71 g., 0.3 mol.) and 130 ml. of ethanol are added to the mixture and it is stirred at 25° for 12 hours. The mixture is evaporated to remove the ethanol and the solid residue is collected by filtration to give methyl 10-sulfodecyldithiocarbamate.

Methyl 10-sulfodecyldithiocarbamate (31.4 g., 0.096 mol.) is reacted with 6.5 g. (0.1 mol.) of sodium azide as described above to give 1-(10-sulfodecyl)tetrazole-5-thiol.

1-(10-sulfodecyl)tetrazole-5-thiol (4.84 g., 15 mmol.) is slowly added to a solution of 3.36 g. (40 mmol.) of sodium bicarbonate in 100 ml. of water. 7β-[syn-2-methoxyimino-2-α-furylacetamido]cephalosporanic acid (10 mmol.) is then added and the mixture is heated at 65° for 3.5 hours. The mixture is filtered, the filtrate is extracted with ethyl acetate and the aqueuos layer is acidified to pH 4 and extracted again with ethyl acetate. The extract is dried (MgSO$_4$) and evaporated to dryness to give 7-[syn-2-methoxyimino-2-furylacetamido]-3-[1-(10-sulfodecyl)tetrazol-5-ylthiomethyl]-3-cephem-4-carboxylic acid.

EXAMPLE 17

When an equivalent amount of an aminosulfonic acid listed below:
  2-aminobutanesulfonic acid
  1-amino-2-methylpropanesulfonic acid
  1-amino-3-methylbutanesulfonic acid
is used in the procedure of Example 14 in place of 2-aminoethanesulfonic acid and the resulting dithiocarbamates are treated with sodium azide as described therein, the following substituted tetrazole thiols are obtained:
  1-(1-sulfomethylpropyl)tetrazole-5-thiol
  1-(2-methyl-1-sulfopropyl)tetrazol-5-thiol
  1-(3-methyl-1-sulfobutyl)tetrazole-5-thiol.

Reaction of a tetrazole thiol listed above with 7-[syn-2-methoxyimino-2-furylacetamido]cephalosporanic acid as described hereinabove gives the corresponding 1-(1-sulfomethyl-propyl), 1-(2-methyl-1-sulfopropyl and 1-(3-methyl-1-sulfobutyl)tetrazole congeners.

EXAMPLE 18

An injectable pharmaceutical composition is formed by adding sterile water or sterile saline solution (2 ml.) to 400 mg. of 7-[syn-2-methoxy-2-α-furylacetamido]-3-[1-sulfaminoethyl) tetrazol-5-ylthiomethyl]-3-cephem-4-carboxylic acid sodium salt.

The composition is administered parenterally preferably intramuscularly from 2-5 times daily to bacterially infected patients.

The other compounds of this invention as described in Examples 1–17 are formulated and used similarly as will be apparent to those skilled in the art.

It will be recognized also that since the main use of the compounds of this invention are as injectable pharmaceutical agents the water soluble forms are most useful as the ultimate end products such as the sodium or potassium salts. The acid forms are of course useful for preparing the salt derivatives or other soluble derivatives. The dosage unit range is from 50-500 mg.

What is claimed is:

1. A compound of the formula:

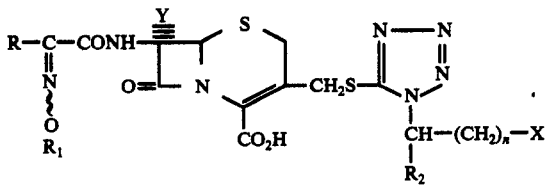

in which:
R is thienyl, furyl or phenyl;
$R_1$ is hydrogen, lower alkyl, benzyl, phenethyl, thienylmethyl or furylmethyl;
$n$ is selected from 0-9;
$R_2$ is hydrogen or methyl;
X is sulfo, sulfamyl, sulfamino or methylsulfonamido; and
Y is hydrogen or methoxy, together with its alkali metal salts.

2. The compound is claim 1 in which the configuration at the imine center is syn.

3. The compound of claim 2 in which R is α-furyl.

4. The compound of claim 2 in which $R_2$ is hydrogen and $n$ is 0-4.

5. The compound of claim 2 in which R is α-furyl, $R_1$ is hydrogen or methyl, Y is hydrogen or methoxy; $R_2$ is hydrogen; $n$ is 0-4 and X is sulfo, sulfamyl, sulfamino or methylsulfonamido.

6. The compound of claim 2 in which X is sulfamino or methylsulfonamido.

7. The compound of claim 1 being 7-[syn-2-methoxyimino-2-α-furylacetamido]-3-[1-(2-sulfaminoethyl)-tetrazol-5-ylthiomethyl]-3-cephem-4-carboxylic acid together with its sodium or potassium salts.

8. The compound of claim 1 being 7-[syn-2-methoxyimino-2-α-furylacetamido]-3-[1-(2-methanesulfonamido)tetrazol-5-ylthiomethyl]-3-cephem-4-carboxylic acid together with its sodium or potassium salts.

9. The compound of claim 1 being 7-(syn-2-hydroxyimino-2-α-furylacetamido)-3-[1-sulfomethyltetrazol-5-ylthiomethyl]-3-cephem-4-carboxylic acid, disodium salt.

10. The compound of claim 1 being 7-[syn-2-methoxyimino-2-α-furylacetamidol]-3-[1-sulfomethyltetrazol-5-ylthiomethyl]-3-cephem-4-carboxylic acid disodium salts.

11. The compound of claim 1 being 7α-methoxy-7β-[syn-2-methoxyimino-2-α-furylacetamido]-3-[1-sulfomethyltetrazol-5-ylthiomethyl]-3-cephem-4-carboxylic acid, disodium salt.

12. The compound of claim 1 being 7α-methoxy-7β-[syn-2-methoxyimino-2-α-furylacetamido]-3-[1-2-sulfaminoethyl)tetrazol-5-ylthiomethyl]-3-cephem-4-carboxylic acid, disodium salt.

13. The compound of claim 1 being 7β-[syn-2-methyoxyimino-2-α-furylacetamido]-3-[1-(2-sulfamylethyl)tetrazol-5-ylthiomethyl]-3-cephem-4-carboxylic acid.

14. The compound of claim 8 in the form of its 4-loweralkanoyloxymethyl esters said lower alkanoyl group having up to 6 carbon atoms.

15. A pharmaceutical composition having antibacterial activity comprising an active but nontoxic quantity of a compound of claim 1 and a pharmaceutically acdeptable carrier.

16. A method of inducing antibacterial activity in an infected patient comprising administering internally to said patient an effective but nontoxic quantity of a compound of claim 1.

17. The method of claim 16 in which the administration is parenterally.

18. The method of claim 16 in which the unit dosage quantity is selected from the range of from about 50-500 mg. of said compound.